United States Patent
Krall et al.

(10) Patent No.: US 8,568,757 B2
(45) Date of Patent: *Oct. 29, 2013

(54) FORMULATIONS EMPLOYING ANHYDROUS DISINFECTANT

(71) Applicant: Pure Bioscience, El Cajon, CA (US)

(72) Inventors: Michael L. Krall, El Cajon, CA (US); Dolana Jonte, El Cajon, CA (US); Richard Gumienny, Jr., El Cajon, CA (US)

(73) Assignee: Pure Bioscience, El Cajon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/677,258

(22) Filed: Nov. 14, 2012

(65) Prior Publication Data

US 2013/0071459 A1 Mar. 21, 2013

Related U.S. Application Data

(63) Continuation of application No. 12/855,609, filed on Aug. 12, 2010, now Pat. No. 8,399,003.

(60) Provisional application No. 61/233,424, filed on Aug. 12, 2009.

(51) Int. Cl.
*A01N 25/34* (2006.01)
(52) U.S. Cl.
USPC ............................ 424/405; 514/495; 424/408
(58) Field of Classification Search
None
See application file for complete search history.

(56) References Cited

U.S. PATENT DOCUMENTS

| 5,824,267 | A | 10/1998 | Kawasumi et al. | |
| 5,916,401 | A * | 6/1999 | Gannon | 156/240 |
| 6,197,814 | B1 | 3/2001 | Arata | |
| 7,732,486 | B2 | 6/2010 | Arata | |
| 2005/0245605 | A1 | 11/2005 | Arata | |
| 2006/0115440 | A1 | 6/2006 | Arata et al. | |
| 2006/0182812 | A1 * | 8/2006 | Ono | 424/604 |
| 2006/0254988 | A1 | 11/2006 | Frampton | |
| 2007/0122462 | A1 | 5/2007 | Chandra et al. | |
| 2007/0185350 | A1 * | 8/2007 | Arata | 562/584 |
| 2008/0156232 | A1 | 7/2008 | Crudden et al. | |
| 2008/0319062 | A1 | 12/2008 | Arata | |
| 2009/0035342 | A1 | 2/2009 | Karandikar et al. | |
| 2009/0130161 | A1 * | 5/2009 | Sarangapani | 424/409 |

FOREIGN PATENT DOCUMENTS

| EP | 1 839 645 | 10/2007 |
| WO | WO-2005/041861 | 5/2005 |
| WO | WO-2006/029213 | 3/2006 |

OTHER PUBLICATIONS

International Search Report and Written Opinion for PCT/US10/45369, mailed Oct. 12, 2010, 6 pages.
Opinion on Citric Acid and Silver citrate, Jan. 21, 2009, retrieved from the Internet: URL:http://ec.europa.eu/health/ph_risk/committees/04_sccp/docs/sccp_o_165.pdf, retrieved on Oct. 25, 2012.
Supplementary European Search Report for EP 10808781.8, mailed Nov. 9, 2012, 10 pages.

* cited by examiner

*Primary Examiner* — Scott Long
*Assistant Examiner* — Sarah Alawadi
(74) *Attorney, Agent, or Firm* — Morrison & Foerster LLP

(57) ABSTRACT

Use of dried compositions of silver dihydrogen citrate along with citric acid in antimicrobial amounts directly as disinfectants is described.

10 Claims, No Drawings

FORMULATIONS EMPLOYING ANHYDROUS DISINFECTANT

CROSS-REFERENCE TO RELATED APPLICATION

This application is a continuation of U.S. Ser. No. 12/855,609 filed 12 Aug. 2010 which claims benefit of provisional application U.S. 61/233,424 filed 12 Aug. 2009. The contents of this document are incorporated herein by reference.

TECHNICAL FIELD

The invention relates to the use of the anhydrous form of silver dihydrogen citrate (SDC) directly, without reconstitution in aqueous liquid, for antimicrobial protection. More specifically, the invention relates to direct use of SDC in non-aqueous compositions.

BACKGROUND ART

The preparation of aqueous solutions of silver dihydrogen citrate (SDC) and citric acid was described in U.S. Pat. No. 6,197,814, incorporated herein by reference. In this method, the SDC is generated electrolytically in a solution of 5-25% citric acid. According to the '814 patent, the resulting aqueous disinfectant may optionally be mixed with alcohol and/or a detergent and can be used on exposed or contaminated surfaces to kill bacteria, virus, fungi and other microorganisms. It can also be used to disinfect wounds and to behave as a disinfectant in water systems, such as cooling towers, hot water systems, potable water systems, etc.

PCT publication WO2005/041861 and U.S. Pat. No. 7,732,486, also incorporated herein by reference, describes preparing an anhydrous form of the SDC/citric acid solution for ease of transport. According to this publication, in order to employ the anhydrous form as a disinfectant, it should be reconstituted to recreate the aqueous systems described in the '814 patent. As noted in the '861 publication and the '486 patent, the anhydrous form is capable of being reconstituted to a fully-active aqueous disinfectant.

It has now been found that reconstitution of this anhydrous form is unnecessary, and that the anhydrous form itself may be employed in non-aqueous systems as an in situ disinfectant and antimicrobial protectant.

DISCLOSURE OF THE INVENTION

In one aspect, the present invention is directed to a method to disinfect a variety of environments, which method comprises employing an anhydrous silver dihydrogen citrate (SDC)/citric acid composition in dry form. For instance, the dry SDC/citric acid may be used as a coating on a surface or as a component of a non-aqueous formulation, such as paint or drywall. The invention is also directed to formulations that comprise an antimicrobial amount of an anhydrous SDC/citric acid composition as part of a non-aqueous formulation.

Typically, the mol ratio of citric acid to SDC in the anhydrous compositions is such that there is a molar excess of citric acid over the SDC, of the order of 5, 10, 15, 20 or 25 to 1. All intermediate values are also included.

This anhydrous composition, then, is employed in the methods and formulations of the present invention.

In order to avoid confusion, the anhydrous SDC/citric acid itself will be referred to as a "composition" and a solid or non-aqueous liquid formulation in which it has been included will be referred to as a "formulation."

MODES OF CARRYING OUT THE INVENTION

A method for obtaining anhydrous SDC/citric acid compositions is described in detail in the above-referenced PCT publication WO2005/01861 and U.S. Pat. No. 7,732,486. Briefly, as therein disclosed, an aqueous solution of SDC in the presence of significant amounts of citric acid is prepared generally according to the process set forth in U.S. Pat. No. 6,197,814, i.e., the SDC is generated by applying either DC or AC current across silver electrodes immersed in a citric acid solution containing, for example, citric acid at a concentration of the order of 1-25% generally 5-20% or 5-10% by weight.

The water is removed from the resulting aqueous disinfectant, preferably by freeze-drying a frozen solution under vacuum effecting sublimation of the water. Other means for removing water from an appropriate SDC/citric acid solution may also be employed, such as vacuum drying, spray drying, or other means of effecting removal of the aqueous solvent so long as the antimicrobial effect of the SDC/citric acid composition is not destroyed.

The anhydrous composition may be milled into suitable particle sizes for application. Any art-recognized means for disaggregating and fluidizing solids may be employed. Typical particle sizes range from 2-500µ, but larger or smaller sizes may also be employed. For medical use, for example, the particles may be in the range of 100-1,000 nm.

"Antimicrobial" includes effective protection against fungi, viruses, bacteria, archaea, and the like. Thus, any infectious agent is included as a "microbial" agent.

"Non-aqueous formulations" refers to formulations that effectively exclude any water component whatsoever, or that include only 5%-15% water by weight or less. They do not include emulsions, lotions, and the like that have substantial amounts of water but rather either are liquid formulations, wherein no more than 5-15% preferably no more than 1-5% by weight is water, or are solid materials of any type. Emulsions and lotions that contain SDC/citric acid are described in PCT publication WO2006/029213 also incorporated herein by reference. However, these formulations are prepared directly from the aqueous solutions of SCD/citric acid. The present invention also includes methods of preparing these compositions or similar compositions using the anhydrous composition per se.

In some embodiments, the anhydrous composition or a formulation containing it ultimately comes in contact with an aqueous environment; in other applications, it does not. In each case, however, the anhydrous SDC/citric acid composition is employed without reconstituting it first into an aqueous solution.

In exemplary, but non-limiting applications, the anhydrous composition is included in various coatings and construction materials, such as paints or other coatings or materials employed to construct solid components such as countertop materials including Formica® and high pressure laminates, drywall, plaster and tile. The use of this material in drywall is especially important to prevent the formation of mold. The anhydrous composition may also directly be used in packaging materials such as paper, cardboard, Styrofoam™, plastics and the like. It may also be used in caulks and sealants as well as in woven and non-woven fabrics including synthetic and natural fabrics.

Depending on the nature of the application, the weight percentage of the anhydrous composition in the finished product will vary over a wide range from about 0.5% by weight to about 50% by weight, typically 1-2% by weight. The anhydrous composition may be incorporated in the manufacture of the product, for example, by mixing the composition directly into paint or varnish or by including it in a preparation of monomers to be polymerized in the formation of polymers or in the particulates pressed into fiberboard. The SDC/citric acid anhydrous composition is compatible with a wide variety of materials and skilled artisans will understand how best to incorporate this composition effectively into non-aqueous systems.

The dried SDC/citric acid composition of the invention is also useful in the context of medical and pharmaceutical applications and can be applied as a dry coating to bandages and medical devices, such as catheters or surgical tools. The dry SDC/citric acid may also be directly applied to wounds, especially wherein deep wounds, internal wounds or subcutaneous infections are a threat. The dry SDC/citric acid can be combined with various other pharmaceuticals in tablets, powders, and the like. Other pharmaceuticals include antibiotics, anti-clotting agents, and effervescing systems.

Anhydrous SDC/citric acid compositions of the invention are also useful directly in water treatment by integrating them with filter media, and employed in solid form in various contexts such as toilet bowl sanitizers, and are also useful in agriculture for crop-dusting either alone or in combination with other dried materials such as fertilizers and herbicides and pesticides.

A non-limiting list of such uses is as follows:

Anhydrous SDC Combined with an Acceptable Substrate to Provide Antimicrobial Protection in Commercial Processes:

Plastics and fiberglass materials (FRP systems)

Woven and nonwoven fabrics: organic and inorganic; filament and monolithic strand Polymers Vinyls Paint: protective coating systems—single and multi-part, e.g. to prevent mold in drywall Latex Architectural finishes, i.e.: Formica®/countertop materials and other high pressure laminates Caulks and conforming sealants Hardening Foams, thermoformed and catalyzed Paper/cardboard packaging and attendant coatings Construction materials: cementitious coatings, drywall and drywall finishing compounds, plaster, tile and tile grouts Anhydrous SDC for Medical and Pharmaceutical Applications:

Combined with antibiotics as a synergizing/potentiating agent

Combined with anti-clotting agents to provide anti-infective properties

Combined with medical powders to be applied as an anti-infective dusting agent for pre and post surgical procedures or trauma wound application Combines with co-valent dry chemistry for use as a biological warfare decontaminant Incorporated into a bandage substrate Tabletized chemistries: effervescing and non-effervescing systems utilizing other actives and excipients Gel and semi-solid suppository delivery systems Medical device coatings Curative/palliative treatment of subcutaneous and deeper internal infections Water Treatment:

Dry algaecide/bactericide

Combined with water treatment resins

Combined with filter media to mitigate microbial growth

Introduced into fluid handling systems for biofilm mitigation

Aquaculture

Agriculture:

Systemic treatment for plant pathogens utilizing various time-release methodologies Surface dusting for plant pathogen prevention/mitigation Soil pH moderator Dry sanitizer for pre-and post-harvest rinse Tabletized unit dosing for process equipment Unit dose ornamental & cut flower preservative Commercial Mass Market:

Dry formed tablet/pelletized home fruit and vegetable wash

Tabletized unit dose home hard surface sanitizer

Toilet sanitizer

Unit dose carpet and upholstery sanitizer systems

The following examples are offered to illustrate but not to limit the invention.

EXAMPLE 1

Preparation of Antimicrobial Drywall

Antimicrobial drywall is prepared by incorporating silver dihydrogen citrate (SDC) in the gypsum core, in or on the paper covering, or in both the gypsum core and paper covering of drywall. The SDC-containing drywall resists the growth of microbes, in particular fungi, when compared to standard drywall.

Antimicrobial drywall containing SDC in the gypsum core is prepared by adding solid SDC to a slurry containing gypsum powder, water, paper pulp, starch and/or set controlling agents, in an amount sufficient to exhibit efficacy against microbes. The resultant gypsum slurry is sandwiched between two sheets of craft paper stock, referred to as the front and back paper facings. The paper with the slurry in between is run through a set of rollers to make it flat and smooth, the edges are shaped, and the drywall is cut to the desired size and dried.

Antimicrobial drywall containing SDC in the paper covering is prepared by spraying one or both of the front and back paper facings with a solution of SDC in an appropriate solvent prior to drying the cut drywall. Alternatively, SDC is applied as a coating on one or both sides of the paper covering before the paper is contacted with the gypsum slurry.

EXAMPLE 2

Preparation of Antimicrobial Paper

A slurry of paper forming fibers prepared according to a wet-laid process is mixed with an aluminum silicate or titanium dioxide filler in a quantity of about 1%-10% parts per weight of fiber. The mixture is stirred constantly with the addition of starch paste as a sizing compound. An interfiber binding agent is prepared by adding solid SDC to latex polyacrylamide or polyvinyl acetate, as a melt or as a solution in a compatible solvent, and mixing to incorporate the SDC within the polymeric matrix. The binding agent mixture is added to the pulp material and mixed, and the mixture is poured onto a wire screen, dewatered, pressed and calendared to obtain a smooth finish.

EXAMPLE 3

Preparation of Antimicrobial Grout

Silver dihydrogen citrate (SDC) is admixed with a standard dry grout compound in an amount sufficient to exhibit efficacy against microbes.

The dry admixture is mixed with water according to packaging instructions and cast into 1-2 inch diameter rounds for testing. The SDC-containing samples resist *Aspergillus niger* (household black mold) relative to control samples lacking SDC when exposed to simulated household shower conditions.

EXAMPLE 4

Preparation of Antimicrobial High Pressure Laminate

SDC is admixed into a conventional melamine formulation, including ceramic reinforcement materials and pigments, in an amount sufficient to exhibit efficacy against microbes. The melamine mixture is spread onto craft paper and dried. The SDC-containing melamine layers are pressed together using conventional heating and pressing equipment to produce a high-pressure laminate material.

The SDC-containing laminate material resists the growth of microbes, including bacteria and fungi, relative to traditional laminates.

EXAMPLE 5

Preparation of Antimicrobial Coated Catheters

An antimicrobial coating composition is prepared by admixing finely ground silver dihydrogen citrate (SDC) with a hexane dispersion of room temperature vulcanized (RTV) silicone resin. The surface of the catheter to be coated is cleaned, and the article is dip-coated by immersing in the SDC-containing mixture for several minutes. The catheter is dipped into the solution 1 to 3 times, until the desired thickness of the coating is achieved. The article is allowed to dry between coatings and then further dried at elevated temperature.

The treated catheter resists the growth of undesirable microbes relative to an untreated control when incubated at 37° C. for 24 to 48 hours with inoculum cultures of test bacteria, such as *E. coli* (e.g., clinical isolate from UTI).

All documents cited herein are incorporated by reference in their entirety.

The invention claimed is:

1. A solid formulation which comprises an antimicrobial amount of an anhydrous composition of SDC and citric acid (citric acid/SDC composition), wherein said anhydrous citric acid/SDC composition comprises no more than 50% by weight of said formulation,
which solid formulation is selected from the group consisting of; fiberglass material; woven or nonwoven fabric; a polymer; vinyl; high pressure laminate; paper/cardboard packaging; cementitious coatings; drywall; drywall finishing compounds; plaster; tile; tile grout, a dry combination with anti-clotting agents to provide anti-infective properties; a dry combination with medical powders to be applied as an anti-infective dusting agent for pre- and post-surgical procedures or trauma wound application; a dry combination with covalent dry chemistry for use as a biological warfare decontaminant: a bandage substrate; a tabletized chemistry; a suppository delivery system; a dry algaecide/bactericide; a dry combination with water treatment resins; a dry combination with filter medium to mitigate microbial growth; a surface dusting for plant pathogen prevention/mitigation; a soil pH moderator; a tabletized unit dosing for process equipment; a unit dose for use as an ornamental and cut flower preservative; tablet formulated for fruit and vegetable wash; a tabletized unit dose home hard surface sanitizer; a pelletized toilet sanitizer; and a unit dose carpet and upholstery sanitizer system.

2. The formulation of claim 1 wherein the citric acid in said anhydrous composition is in molar excess of the SDC.

3. The formulation of claim 1 wherein said anhydrous composition is in the form of microparticles.

4. The formulation of claim 3 wherein the microparticles have average diameters of 2-500 μM.

5. The formulation of claim 1 wherein the percentage by weight of said anhydrous citric acid/SDC composition is 0.5-50% by weight.

6. The formulation of claim 1 wherein said solid formulation is a construction material, a solid polymer or a paper product.

7. The formulation of claim 5 wherein the construction material is drywall.

8. The formulation of claim 1 wherein the solid formulation is in the form of a tablet.

9. The formulation of claim 5 which is a paper product.

10. The formulation of claim 3 wherein the solid formulation is selected from the group consisting of plastic; countertop material; and construction material.

\* \* \* \* \*